United States Patent
De La Fuente et al.

(10) Patent No.: US 7,498,177 B2
(45) Date of Patent: Mar. 3, 2009

(54) QUANTUM DOTS AND THEIR USES

(76) Inventors: Jesus Martinez De La Fuente, c/Pinton Saló 8, 2° C, Córdoba (ES) 14010; Catherine Cecilia Berry, 14 Barra St., Maryhill Park, Glasgow (GB) G20 0AZ; Mathis Riehle, 87 Norse Road, Glasgow (GB) G149EF; Leroy Cronin, 67 Antermony Rd, Glasgow (GB) G66 8AA; Adam Sebastian G. Curtis, 2 Kirklee Circus, Glasgow (GB) G12 0TW ( * ) Notice: Subject to any disclaimer, the term of this patent is extended or adjusted under 35 U.S.C. 154(b) by 7 days.

(21) Appl. No.: 11/409,645

(22) Filed: Apr. 24, 2006

(65) Prior Publication Data

US 2007/0249064 A1    Oct. 25, 2007

(51) Int. Cl.
 *G01N 33/551*    (2006.01)
 *G01N 33/553*    (2006.01)

(52) U.S. Cl. .......................... 436/524; 435/6; 436/172; 436/518; 436/525; 436/805

(58) Field of Classification Search ................ None
See application file for complete search history.

(56) References Cited

U.S. PATENT DOCUMENTS 5,989,921 A * 11/1999 Charlton et al. ............. 436/501
6,306,610 B1 * 10/2001 Bawendi et al. ............. 435/7.1
2004/0058457 A1 * 3/2004 Huang et al. ................ 436/524
2005/0208142 A1 * 9/2005 Zheng et al. ................ 424/489

OTHER PUBLICATIONS

Alivisatos, Paul, "Colloidal quantum dots. From scaling laws to biological applications", Pure Appl. Chem., 72: 3-9 (2000).
Berry, Catherine et al., "Dextran and albumin derivatised iron oxide nanoparticles: influence on fibroblasts in vitro", Biomaterials, 24: 4551-4557 (2003).
Denneberg, T. et al., "Alternative Treatment of Cystinuria with alpha-Merkaptopropionylglycine, Thiola", Proc. Eur. Dial. Transplant. Assoc., 20: 427-433 (1983).
Gleiter, Herbert, Adv. Materials, 4: 474-481 (1992).
Gupta, Ajay et al., "Receptor-Mediated Targeting of Magnetic Nanoparticles Using Insulin as a Surface Ligand to Prevent Endocytosis", IEEE Transaction of Nanobioscience, 2(4): 255-261 (2003).
Huang, Tao et al., "Luminescence of Tiopronin Monolayer-Protected Silver Clusters Changes to that of Gold Clusters upon Galvanic Core Metal Exchange", J. Phys. Chem. B, 107: 7434-7440 (2003).

(Continued)

*Primary Examiner*—Christopher L Chin
(74) *Attorney, Agent, or Firm*—Dann, Dorfman, Herrell and Skillman, P.C.; Patrick J. Hagan

(57) ABSTRACT

Quantum dots having ligands that comprise tiopronin capping groups are disclosed, along with a method for their preparation. The biocompatibility of these quantum dots is also demonstrated. The functionalization of the quantum dots of the present invention with targeting groups is also described using the example of a translocation peptide that allows the quantum dots to penetrate into the nucleus of cells.

32 Claims, 5 Drawing Sheets

OTHER PUBLICATIONS

Spanhel, Lubomir et al., "Photochemistry of Colloidal Semiconductors. 20. Surface Modification and Stability of Strong Luminescing CdS Particles", J. Am. Chem. Soc., 109: 5649-5655 (1987).

Detar, DeLos et al., "Reactions of Carbodiimides. I. The Mechanisms of the Reactions of Acetic Acid with Dicyclohexylcarbodiimide", J. Am. Chem. Soc., 88: 1013-1019 (1966).

Mitchell, Gregory P. et al., "Programmed Assembly of DNA Functionalized Quantum Dots", J. Am. Chem. Soc., 121: 8122-8123 (1999).

Templeton, Allen C. et al., "Redox and Fluorophore Functionalization of Water-Soluble, Tiopronin-Protected Gold Clusters", J. Am. Chem. Soc., 121: 7081-7089 (1999).

Mattoussi, Hedi et al., "Self-Assembly of CdSe-Zns Quantum Dot Bioconjugates Using an Engnieered Recombinant Protein", J. Am. Chem. Soc., 122: 12142-12150 (2000).

Hostetler, Michael J. et al., "Alkanethiolate Gold Cluster Molecules with Core Diameters from 1.5 to 5.2 nm: Core and Monolayer Properties as a Function of Core Size", Langmuir, 14: 17-30 (1998).

Bruchez, Marcel et al., "Semiconductor Nanocrystals as Fluorescent Biological Labels", Science, 281: 2013-2016 (1998).

Chan, Warren et al., "Quantum Dot Bioconjugates for Ultrasensitive Nonisotopic Detection", Science, 281: 2016 (1998).

* cited by examiner

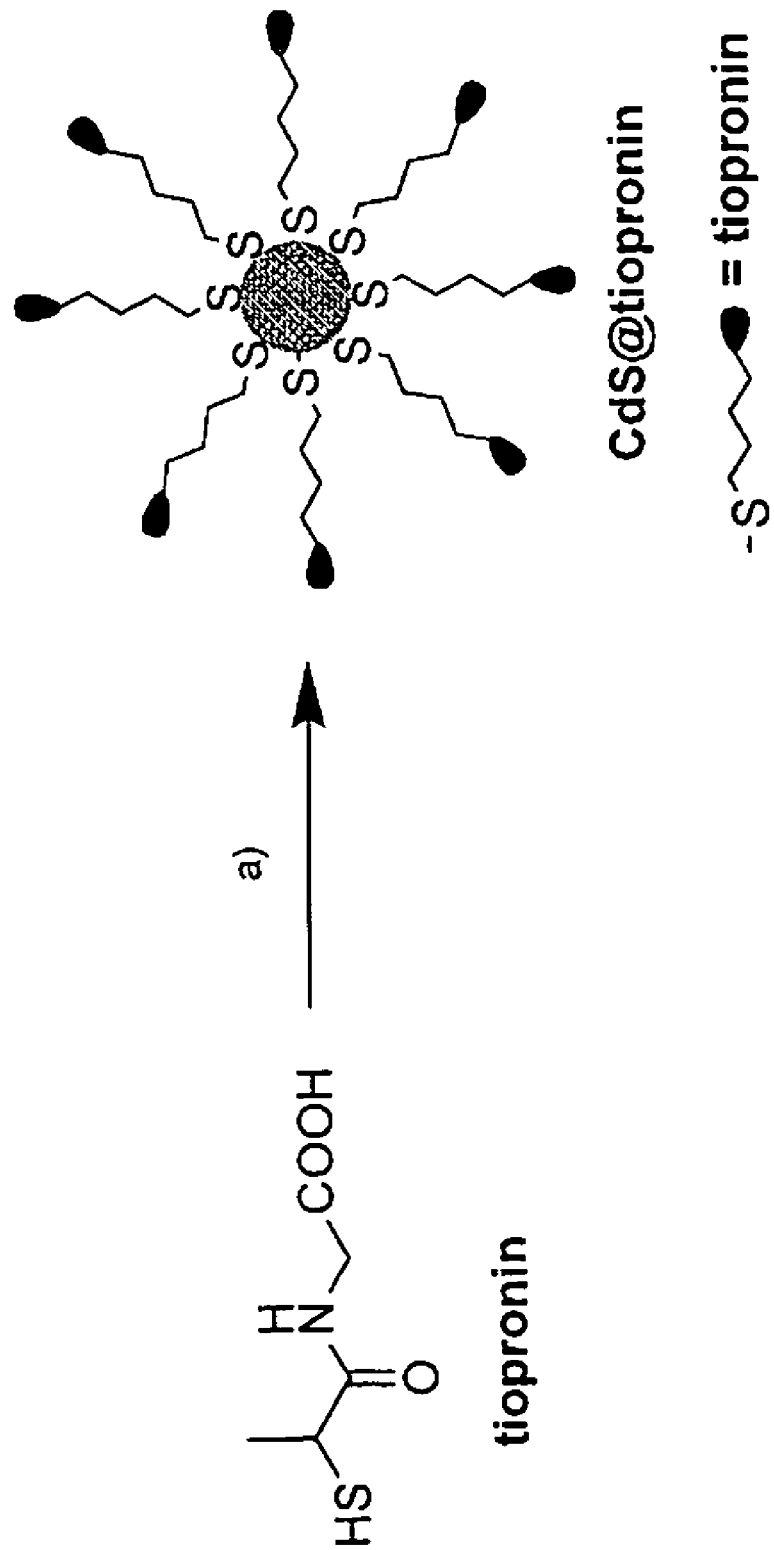

Figure 2. Cytotoxicity profiles of CdS@tiopronin QDs when incubated with human fibroblasts as determined by MTT assay. Percentage of viability of fibroblasts was expressed relative to control cells (n = 3). Results are represented as mean ± standard deviations.

QUANTUM DOTS AND THEIR USES

FIELD OF THE INVENTION

The present invention concerns quantum dots and their uses, in particular for labelling in biological systems. The present invention also provides methods of making quantum dots.

BACKGROUND OF THE INVENTION

In modern biological analysis, various kinds of organic dyes are used. Among the most common types are fluorescent dyes. However, today more flexibility and demands are placed on these dyes. In addition, fluorescent dyes suffer from the disadvantage that the signal emitted by the fluorophors has a short lifetime which often necessitates continuous excitation by a laser. The requirement to excite the fluorophors at the same time as detecting the signal they emit in turn places considerable demands on the equipment needed to detect the fluorophors.

Nanocrystals of semiconducting materials, otherwise known in the art as quantum dots, have fascinated physicists, chemists and electronic engineers since the 1970s. The most striking feature of these materials is that their chemical and physical properties differ markedly from those of the bulk solid.[1] Now that their quantum size effects are understood, fundamental and applied research on these systems has become increasingly popular. An interesting application is the use of nanocrystals as luminescent labels for biological systems.[2-5] The quantum dots have several advantages over conventional fluorescent dyes: quantum dots emit light at a variety of precise wavelengths depending on their size and have long luminescent lifetimes.

While quantum dots possess these advantages over traditional fluorescent dyes, considerable challenges remain to be addressed concerning their stability and toxicity that limits their widespread use in biological systems. It also remains a problem to produce quantum dots that can be derivatised or coupled to biological species to make them useful in such studies.

Furthermore, numerous methods exist for the syntheses of semiconductor nanocrystals, but most processes are costly, require sophisticated equipment or extreme reaction conditions, and result in low product yields.[2,3,4,6] These synthetic methods are impractical for applications requiring larger quantities or higher concentrations of nanocrystals. Many of the conditions used in the manufacture and application of the quantum dots of the prior art have been incompatible with biological species.

SUMMARY OF THE INVENTION

Broadly, the present invention relates to quantum dots that comprise semiconductor cores to which a plurality of ligands are covalently linked, and in particular to quantum dots having ligands comprising a tiopronin group as a capping group.

In some embodiments, the semiconductor core of the quantum dots is formed from a metal sulphide, for example cadmium sulphide (CdS), zinc sulphide (ZnS) or lead sulphide (PbS). Preferably, the semiconductor core of the quantum dot is formed from cadmium sulphide (CdS).

As discussed below, the mean diameter of the quantum dot (i.e. the semiconductor core capped with the tiopronin group) may be varied, in particular to modify the properties of the quantum dots, most importantly the wavelength at which the quantum dot emits radiation after excitation. In general, the quantum dots have mean diameters between about 1 to 15 nm, and more preferably mean diameters between about 2 nm and about 5 nm. Quantum dots in these general size ranges, such as the quantum dots with cadmium sulphide (CdS) cores disclosed herein, emit light at a wavelength between about 400 nm and about 900 nm and have an excitation wavelength of between about 250 nm and 600 nm. More preferably, the quantum dots emit light at a wavelength between about 400 nm and 700 nm, more preferably between about 450 nm and about 650 nm and most preferably emit light between about 500 nm and 600 nm. The exemplified quantum dots with cadmium sulphide (CdS) cores emit light at about 550 nm and have an excitation wavelength of about 350 nm to 400 nm. More preferably, these quantum dots have an excitation wavelength of about 385 nm.

In general, one problem in the prior art is that quantum dots were insufficiently stable to be employed in biological labelling reactions. However, generally speaking, the quantum dots of the present invention sufficiently stable for such applications, for example by being stable for at least 6 months, and more preferably at least a year. Conveniently, this can be achieved by storing the quantum dots in a lyophilized composition. When storing the quantum dots, their stability can be improved by storage in the absence of light and at reduced temperature, for example at 4° C.

Accordingly, in a further aspect, the present invention provides a composition comprising a population of quantum dots as described herein. The quantum dots in the composition may be provided in a carrier, e.g. in a solvent such as water or alcohol. Alternatively, as described above, the composition may be lyophilized for storage.

Preferably, the quantum dots of the present invention have the further property that they are water dispersable, thereby facilitating their use in biological systems.

Tiopronin may be represented by the formula:

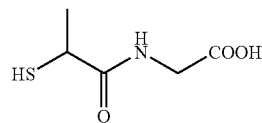

Thus, in the reaction to produce the quantum dots, the thiol group of the tiopronin becomes covalently linked to the semiconductor core of the quantum dot via formation of a metal-sulphide bond, e.g. a Z-S bond where Z is Cd, Zn or Pb, thereby producing the tiopronin capping group. This means that the tiopronin capping group comprises a carboxyl group through which a targeting group may be covalently linked via a coupling reaction, or which can be the subject of further reactions to modify the carboxyl group to another functional group and/or coupled to another moiety.

Although the exemplified quantum dots comprise ligands with tiopronin capping groups, the chemistry disclosed herein is compatible with producing quantum dots having at least one further species of ligand present. By way of example, such further ligands could be introduced at the time of synthesizing the quantum dots, for example by including thiol derivatised forms of them in the reaction mixture so that they become covalently linked to the semiconductor core in the self assembly reaction.

Preferably, the ligands comprising the tiopronin groups are linked to a targeting group. A wide range of targeting groups are know in the art and examples are discussed further below.

The targeting group may be a protein, a peptide, an antibody, a carbohydrate, a glycolipid, a glycoprotein, a chemical compound or a nucleic acid sequence. The targeting group may direct the quantum dot to a tissue type, a cell type, a cellular organelle, a binding partner such as a cell surface receptor or a ligand, a nucleic acid sequence, or an infectious agent. In one embodiment, the targeting group is a translocation signal, such as a TAT peptide.

In preferred embodiments, the present invention provides quantum dots that can be produced by a simple method that is capable of yielding gram-quantities of water-dispersable and stable quantum dots. Accordingly, in a further aspect, the present invention provides a method of making composition of quantum dots comprising metal sulphide cores, wherein the metal sulphide is selected from the group consisting of cadmium sulphide, zinc sulphide and lead sulphide, to which a plurality of ligands are covalently linked, wherein the ligands comprise a tiopronin group, the method comprising mixing sodium sulphate, an aqueous solution of tiopronin and the metal nitrate, thereby producing the quantum dots in a self-assembly reaction in which thiol groups of the tiopronin covalently link to the semiconductor cores via metal-sulphide bonds.

The method may be a single-step procedure. Preferably, the mixing step is carried out at room temperature. The method may also comprise a reaction to couple a ligand to the free carboxyl group of the tiopronin groups, for example coupling a targeting group to the carboxyl group of the tiopronin. By way of example, the carboxyl group of the tiopronin group may be coupled to a reactive amine group of the targeting group, e.g. that is present on a peptide, protein or nucleic acid ligand. Preferred coupling conditions include the use of a carbodiimide coupling reaction in the presence of N-[3-(dimethylaminopropyl]-N'-ethylcarbodiimide hydrochloride (EDC), and optionally N-hydroxysuccinimide (NHS).

The work described herein also demonstrates the biocompatibility the quantum dots of the present invention in examples employing human fibroblasts.

In a further aspect, the quantum dots of the present invention may be employed in a method of detecting a component of a biological system, the method comprising:
 (a) providing in the biological system a composition of quantum dots, the quantum dots comprising a semiconductor core to which a plurality of ligands are covalently linked, wherein the ligands comprise a tiopronin capping group linked to a targeting group that is capable of interacting with the component of the biological system;
 (b) exposing the biological system to radiation at an excitation wavelength of the quantum dots;
 (c) detecting radiation emitted by the quantum dots at their emission wavelength thereby to detect the component in the biological system.

In another aspect, the quantum dots of the present invention may be employed in a method of detecting a targeting group in a biological system, the method comprising:
 (a) providing in the biological system a composition of quantum dots, the quantum dots comprising a semiconductor core to which a plurality of ligands are covalently linked, wherein the ligands comprise a tiopronin capping group linked to a targeting group;
 (b) exposing the biological system to radiation at an excitation wavelength of the quantum dots;
 (c) detecting radiation emitted by the quantum dots at their emission wavelength thereby detecting the targeting group in the biological system.

A quantum dot comprising a targeting group may be used for detecting the targeting group within a biological system, i.e. to determine where the targeting group would naturally be located within a biological system when not coupled to a quantum dot. Therefore, a quantum dot comprising a targeting group may be used as an alternative to tags such as green fluorescent protein. The quantum dots comprising targeting groups may therefore be used to follow real time movement of a targeting group within a biological system. Further, a quantum dot comprising a targeting group may be used for detecting a binding partner of the targeting group within a biological system or a biological sample. Quantum dots comprising targeting groups may therefore be used to follow real time interactions between the targeting group and a binding partner. Biological systems may be, but are not limited to, plants, animals, tissues, cell types, cell cultures, cells, cellular organelles, viruses, protozoa, fungi and prions. Examples of organelles include, but are not limited to, the nucleus, the mitochondria and chloroplasts. In one embodiment, a quantum dot comprising a targeting group may be used in immunoassays, hybridization assays, cytometry or imaging.

In further aspect, the present invention provides a method of labelling a component of a biological system, the method comprising contacting the component of the biological system with a composition of quantum dots, the quantum dots comprising a semiconductor core to which a plurality of ligands are covalently linked, wherein the ligands comprise a tiopronin capping group linked to a targeting group, wherein the targeting group is capable of binding to or associating with the component of the biological system thereby to label it.

A quantum dot comprising a targeting group may also be used in the preparation of a composition for use in the diagnosis of a disease. Examples of diseases include cancer, infectious diseases, autoimmune diseases, mental disorders and genetic diseases.

Embodiments of the present invention will now be described by way of example and not limitation with reference to the accompanying figures.

BRIEF DESCRIPTION OF THE FIGURES

Scheme 1. Preparation of CdS@tiopronin: a) Cd(NO$_3$)$_2$ 4H$_2$O, Na$_2$S, pH 10, H$_2$O.

DETAILED DESCRIPTION

Quantum Dots

Figure 1:
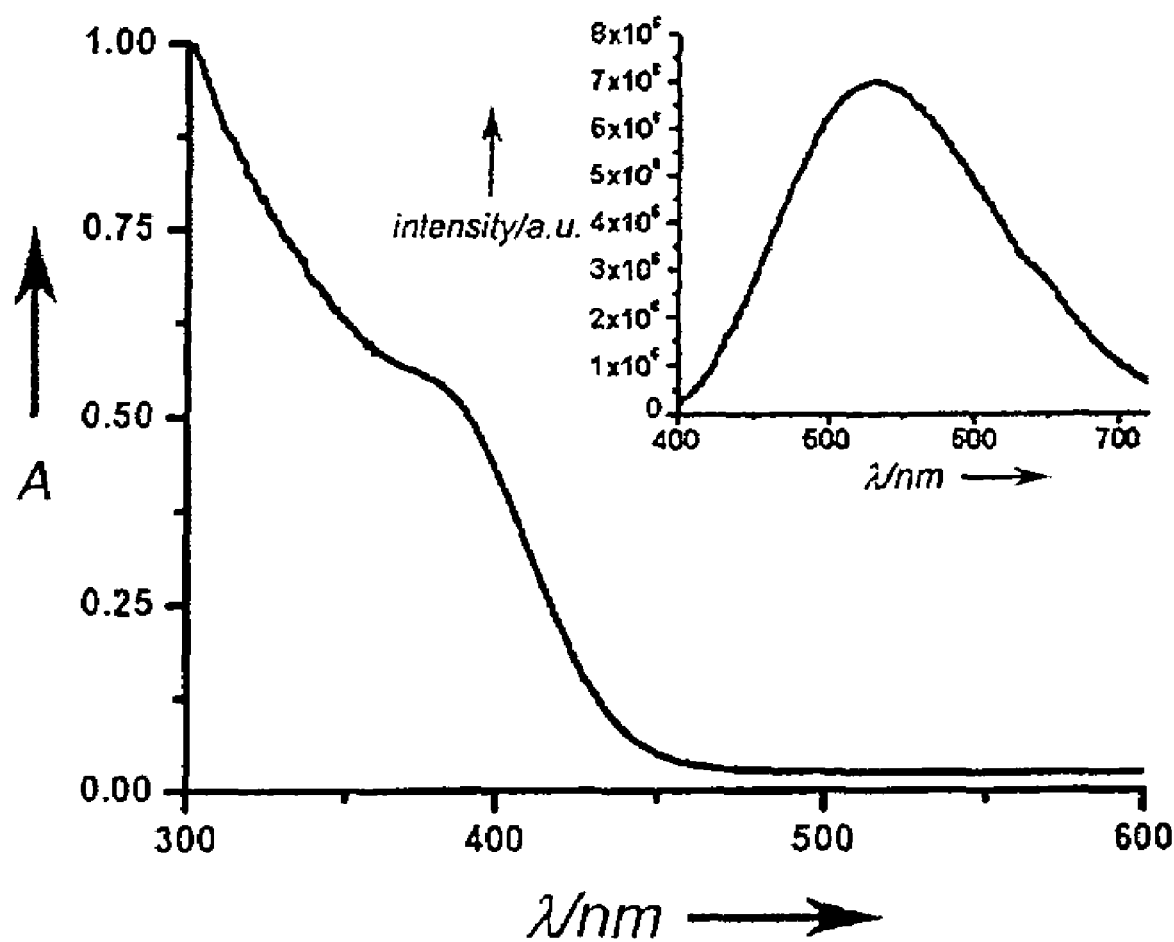
FIG. 1. UV-Vis (outset) and fluorescence spectra (inset) ($\lambda_{exc}$=380 nm) spectrum of CdS@tiopronin in water.

Quantum dots are also known as a semiconductor nanocrystal and are formed from crystals of semiconductor materials having a size in the nanometer range. Preferred quantum dots according to the present invention have cores having mean diameters of less than about 20 nm, more preferably less than about 15 nm and most preferably between about 2 and about 5 nm. Mean diameters of the quantum dots can be measured using techniques well known in the art such as transmission electron microscopy. The most striking property of quantum dots is that they emit fluorescence following exposure to exciting radiation, most usually ultraviolet light. This effect arises because quantum dots confine electrons, holes, or electron-hole pairs or so-called excitons to zero dimensions to a region on the order of the electrons' de Broglie wavelength. This confinement leads to discrete quantized energy levels and to the quantization of charge in units of the elementary electric charge. Quantum dots are particularly significant for optical applications due to their theoretically high quantum yield. Thus, compared to the conventional use of fluorescent labels that need to be continuously excited to produce fluorescence and therefore require complicated or expensive equipment for excitation and detection, the long lived radiation produced from quantum dots is advantageous for applications in which they are used as labels. Thus, the energy levels of small quantum dots can be probed by optical spectroscopy techniques.

In addition, quantum dots have the further advantage that their energy levels, and hence the frequency of the radiation they emit, can be controlled by changing features such as the material from which the quantum dot is made, the size of the quantum dot and the shape of the quantum dot. Generally, quantum dots emit light in visible wavelengths that can be seen by the unaided eye. While the material from which the quantum dot is formed has an effect on the wavelength of the light it emits, the size of the quantum dot usually has a more significant effect on the wavelength of light it emits and hence its visible coloration. In general, the larger quantum dots emit light towards the red end of the spectrum, while smaller quantum dots emit light towards the blue end of the spectrum. This effect arises as larger quantum dots have energy levels that are more closely spaced. This allows the quantum dot to absorb photons containing less energy, i.e. those closer to the red end of the spectrum.

Tiopronin

Tiopronin is a non-natural amino acid having the systematic name N-2-mercaptopropionylglycine. It is a pharmaceutically important drug used for the treatment of cystinuria and rheumatoid arthritis. [7] Importantly, in the context of the present invention, tiopronin has a thiol group through which the tiopronin capping group is capable of being covalently linked to the semiconductor core of the quantum dot via formation of a metal-sulphide bond. In addition, tiopronin also has a free terminal carboxyl group ($—CO_2H$) that provides a handle for further reactivity, for example permitting the coupling of targeting groups to the quantum dots, e.g. for use in biological labelling. Thus, tiopronin provides the quantum dots of the present invention with a surprising level of stability while providing functional groups that enable the quantum dots to be modified for use in a wide range of applications, especially in biological systems.

In a preferred embodiment employing CdS quantum dots nanocrystals, functionalized and protected with the non-natural aminoacid tiopronin, as tools for targeting specific cell sites. Tiopronin has been successfully used as capping agent to protect gold and silver nanoparticles. [8,9] The thiol group of the tiopronin is directly attached to the nanocrystalline semiconductor core of the quantum dots. The tiopronin acts as the stabilizer which helps to control particle size and aggregation, as well as optionally further providing the quantum dots with water solubility and active functional groups suitable for derivatisation and labelling.

Ligands

In general, the quantum dots of the present invention have ligands that comprise the tiopronin capping group to which an optionally further moiety such as a targeting group may be coupled. The further moiety may be a ligand as discussed below. However, in alternative embodiments of the present invention, in addition to the ligands comprising a tiopronin capping group, one or more further species of ligands may be linked to the semiconductor core of the quantum dots. These ligands may comprise (a) one or more carbohydrate groups, such as a polysaccharide, an oligosaccharide or a single saccharide group, and/or (b) a glycoconjugate such as a glycolipid or a glycoprotein, and/or (c) one or more peptides, proteins or fragments thereof, (d) a lipid group, (e) a drug or a prodrug, and/or (f) a nucleic acid molecule, such as a DNA segment, a single or double stranded nucleic acid molecule, a single or double stranded RNA molecule, a RNA molecule having from 17 to 30 ribonucleotides for use in RNA interference methods.

The quantum dots may have more than one species of ligand immobilised thereon, e.g. 2, 3, 4, 5, 10, 20 or 100 different ligands. Alternatively or additionally a plurality of different types of quantum dots can be employed together. Both of these approaches allow the quantum dots to provide a plurality of different functions, for example at a site where they interact with other species. Ligands with multiple attachment sites may be linked to a plurality of nanoparticle cores, e.g. 2, 3, or 4 particles. An example of this would be quantum dots cores linked to the ends of polypeptides or nucleic acid molecules.

In preferred embodiments, the mean number of ligands linked to an individual quantum dot core is at least 20 ligands, more preferably at least 50 ligands, and most preferably 60 ligands.

Targeting Groups

As mentioned above, the tiopronin group provides a free terminal carboxyl group ($—CO_2H$) that enables the quantum dots to associate with or be coupled to other species. A useful class of species that can be coupled to the tiopronin groups are targeting groups. Targeting groups can be used to specifically direct the quantum dots to components of biological systems so that the quantum dots act as labels to enable the components to be detected. Targeting groups may be proteins, peptides, antibodies, carbohydrates, glycolipids, glycoproteins, chemical compounds or nucleic acid molecules. A preferred type of targeting group are small peptides, preferably from 3 to 20 amino acids, and more preferably from 4 to 15 amino acids in length.

In these aspects of the present invention, the biological systems may be an in vivo biological system, e.g. in a living organism, or an in vitro biological system, e.g. a sample of cells. In both cases, the quantum dots have the useful property demonstrated herein that they are substantially non cytotoxic.

The targeting group may cause the quantum dots to directly interact with the component of the biological system, for example when the component of the biological system is one member of a specific binding pair and the targeting group is the second member of the specific binding pair, so that the members of the specific binding pair are capable of binding in the biological system. Examples of specific binding pairs include antibodies and antigens, ligands and receptors, enzymes and substrates, nucleic acid molecules having complementary sequences, and glycoconjugates and glycoproteins. Preferred examples of targeting groups and their specific binding pairs include targeting groups that are ligands capable of binding cell surface receptors, antibodies capable of specifically binding antigens, and neoglycoconjugates binding glycoproteins.

In an alternative embodiment, targeting groups have the more general property of directing the quantum dots to a general part of the biological system. Examples of such targeting groups are peptides known in the art as translocation signals, localisation signals or signal sequences. Examples of such targeting groups and their properties are discussed in Ye et al, Pharmaceutical Research, 19(9): 1302-1309, 2002, and in references cited therein, all of which are expressly incorporated by reference.

These sequences are often derived from proteins from a variety of sources. They are generally amino acid sequences at one end of a native protein that functions like a postal code on the protein for the target organelle. Typically, these peptides are 20 amino acids or less in length, more usually 15 amino acids or less in length and most usually between 4 and 12 amino acids in length. Signal sequences may be used as targeting groups to direct the quantum dots to specific cellular organelles. Examples of such signal sequences include mitochondrial targeting sequences, which are rich in positively charged and hydroxylated amino acids, and generally comprise of 3 to 5 non consecutive Arg or Lys amino acid residues, often in combination with the amino acid residues Ser and/or Thr. Other examples include the peroxisomal targeting signals 1 and 2 which generally comprise a tripeptide from the consensus sequence S/T/A/G/C/N-K/R/H-L/I/V/M/A/F/Y, see for example Swinkels et al, FEBS Letters, 305(2):133-6, 1992.

Other targeting groups are nuclear localization signals (NLS) which are used in cells to target proteins to the nucleus and which therefore may be used as targeting groups to produce the same effect with the quantum dots. These signals are not restricted to proteins encoded within a cell but have also been found in, for example, viral proteins. Typically, an NLS consists of short sequences of positively charged amino acids, e.g. from 4 to 12 amino acids, and which generally comprise Arg or Lys amino acid residues. Examples of common NLS sequences are domain derived from viral Tat proteins, such as HIV Tat. Examples of such peptides include PPKKKRKV, RQARRNRRRRWR and GRKKRRQRRR, the Tat protein derived sequence used in the examples.

The peptides and protein include the transport peptides and proteins include the herpes simplex virus 1 protein VP22, or a functional fragment thereof, see Elliott et al, *J. Virol.* 69: 7932-7941, 1995; Penetratin™, a 16 amino acid peptide available QBiogene having the amino acid sequence KKWK-MRRNQFWVKVQRG that was originally derived from the third α-helix of Antennapedia and which can be employed to introduce species into the cytoplasm or the nucleus of cells, see Dom et al, NAR, 31(2): 556-561, 2003 which discloses Penetratin™, and mutants, retro- and enantio- and retro-inverso forms thereof; or TranIT™, a histone based polyamine available from Mirus, Madison, Wis.

Nucleic acid molecules for use as targeting groups may be double or single stranded DNA, or double or single stranded RNA, such as a RNA molecule having from 17 to 30 ribonucleotides for use in RNA interference methods. The nucleic acid sequences may designed to anneal to a specific target sequence either within a biological system or within a biological sample, e.g. for use in hybridization assays.

Antibodies may be used as targeting groups to detect proteins in biological systems or biological samples. They could be used in similar ways as fluorescent antibody conjugates are used in the art, e.g. in imaging techniques such as fluorescent microscopy or immunoassays such as Enzyme-Linked Immunosorbent Assays (ELISAs). Quantum dots comprising suitable targeting groups, such as antibodies, may also be useful in cytometry, using for example Fluorescence Activated Cell Sorters (FACS). These techniques/applications may benefit from the stability of the quantum dots.

In the present invention, where the targeting group is an antibody, this term describes an immunoglobulin whether natural or partly or wholly synthetically produced. The term also covers any polypeptide or protein comprising an antibody binding domain. Antibody fragments which comprise an antigen binding domain are such as Fab, scFv, Fv, dAb, Fd; and diabodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A.

Antibodies can be modified in a number of ways and the term "antibody molecule" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023 A.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (PCT/US92/09965) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

Quantum dots comprising suitable targeting groups may be used in the preparation of a composition for use in the diagnosis of a disease or for the identification of a disease marker. The disease may be an animal disease, such as a human disease or a plant disease. Examples of diseases that may be diagnosed using quantum dots modified with suitable targeting groups include cancer (e.g. specific types of cancer), infectious diseases, autoimmune diseases, mental disorders, and/or genetic diseases. Diagnosis may take place on a biological sample obtained from the diseased organism, or may be carried out in vivo, e.g. in imaging studies.

EXAMPLES

Preparation of CdS@tiopronin

Cadmium nitrate tetrahydrate (200 mg, 0.6 mmol, 1 eq) and N-(2-mercatopropionyl)glycine) (140 mg, 0.9 mmol, 1.3 eq) were dissolved in previously degassed water (25 mL). The pH of this solution was adjusted to 10 with 1 M $NaOH_{aq}$. After adding dropwise a solution of sodium sulphide (0.05 mg, 0.6 mmol, 1 eq) in degassed water (1 mL), the mixture was stirred for 20 min. The crude CdS@tiopronin was water-soluble. The yellow product was purified by precipitation out of EtOH and lyophilized (168 mg). IR (KBr): ν=3436, 2921, 2855, 1625, 1386, 1297, 1260, 1019 $cm^{-1}$; $^1$H-NMR (400 MHz, $D_2O$): δ=4.70; (s, 2H, $CH_2$), 3.64; (m, 1H, S—CH), 1.32; (d, 3H, $CH_3$, J=7.0 Hz); UV/Vis ($H_2O$): ν=380 nm; Fluorescence ($H_2O$), $\lambda_{exc}$=380 nm, $\lambda_{em}$=540 nm.

Preparation of CdS@tiopronin-Tat

CdS@tiopronin (2.5 mg), (N-(3-dimethylaminopropyl)-N'-ethylcarbodiimide hydrochloride (EDC) (0.20 mg, 1 μmol) and N-Hydroxysuccinimide (NHS) (0.3 mg, 2.3 μmol) were dissolved in previously degassed 2-(N-morpholino) ethanesulfonic acid (MES) (3 mL, 50 mM, pH 6.5). After stirring for 30 min, Tat protein-derived peptide sequence (GRKKRRQRRR) (0.07 mg, 0.05 μmol) was added and left for reacting for 1 h. The yellow product was purified by precipitation out of EtOH and lyophilized (1.6 mg). IR (KBr): ν=3419, 2917, 2842, 2357, 1634, 1385, 1310, 1111, 1024 $cm^{-1}$; UV-Vis ($H_2O$): ν=380 nm; fluorescence ($H_2O$) $\lambda_{exc}$=380 nm, $\lambda_{em}$=540 nm Cell Viability Staining Using Calcein AM/Ethidium Homodimer hTERT-BJ1 human fibroblasts (10000 cells) were seeded onto 22 mm glass coverslips in a culture plate. After 24 h, cell medium was exchanged with fresh medium containing different concentrations of quantum dots, and the cells were cultured at 37° C. in 5% $CO_2$ for 24 h. Subsequently, the medium was removed and the cells were washed with PBS followed by adding calcein AM and ethidium homodimer (2 and 4 μM, Molecular Probes, Leiden, The Netherlands, respectively). After 1 h at 37° C. in 5% $CO_2$, the samples were viewed on a fluorescence microscope.

MTT Assay

HTERT-BJ1 cells (10000 cells) were cultivated in a 96 well plate at 37° C. in 5% $CO_2$. After 24 h the medium was replaced with fresh medium containing the quantum dots in varying concentrations. After cultivating again for 24 h, MTT dye solution (20 μL, 5 mg/mL in PBS) was added to each well. After 3 h of incubation at 37° C. and 5% $CO_2$ the medium was removed, the cells washed with PBS and formazan crystals were dissolved in DMSO (100 μL). The absorbance of each well was read on a microplate reader (Dynatech MR7000 instruments) at 550 nm. The spectrophotometer was calibrated to zero absorbance, using culture medium without cells. The relative cell viability (%) related to control wells containing cell culture medium without quantum dots was calculated by $[A]_{test}/[A]_{control} \times 100$.

Cell Culture

Infinity telomerase-immortalized primary human fibroblasts (hTERT-BJ1, Clonetech Laboratories, Inc., Hampshire, U.K.) suspension ($1 \times 10^5$ cells in 1 mL) were mixed with QDs solution (100 μL, 0.5 mg/mL) for 15 min at 37° C. Then the mixture was centrifuged and the cell pellet was resuspended with fresh medium (3 mL). The cells were seeded onto 22-mm glass coverslips in a 6-well plate for 24 h (37° C., 5% $CO_2$). Before using the samples, the cells were washed with PBS buffer and then fixed in a parafolmaldehyde water solution (4% formaldehyde, 1 mM $NaBH_4$ in PBS) for 15 min. The fixed cells were again washed several times with PBS solution, three times with water and then once with MES buffer. The cover slips were put on a slide and sealed to prevent the samples from drying out. The samples were viewed on a fluorescence microscope using FITC-LP filter.

Results

Synthesis of Quantum Dots Having Tiopronin Ligands

The experiments described above produced in a single step procedure CdS nanocrystals, functionalized and protected with the non-natural aminoacid tiopronin. The examples also demonstrate their utility as biological targeting reagents, in particular that are directed to specific sites in cells. The thiol group of the tiopronin directly attached to the CdS nanocrystals. Tiopronin acted as the stabilizer controlling particle size and aggregation and provided, at the same time, water solubility and active groups for specific labelling.

The functionalized CdS nanocrystals were obtained by adding sodium sulphide to a water solution of tiopronin and cadmium nitrate at room temperature using a modification of the procedure of Spanhel et al.[10] The CdS@tiopronin quantum dots (Scheme 1) thus prepared gave a yellow solution and under ultraviolet illumination (λ=360 nm) emitted light in the green region (550 nm).

The molecules have been purified by precipitation with ethanol and characterized by $^1$H-NMR, FT-IR, UV-Vis and Fluorescence spectroscopy. After lyophilization the CdS@tiopronin was water-soluble and stable for a year in the absence of light at 4° C.

The UV-Vis absorption spectra and the fluorescence emission spectra for CdS@tiopronin are shown in FIG. 1. The UV-Vis spectra of these QDs showed an excitonic transition with a band gap energy ($E_g$) at 3.22 eV (385 nm). The emission spectra of the CdS@tiopronin particles presented a band at 540 nm when the excitation wavelength was 380 nm.

Biological Studies

Figure 2:
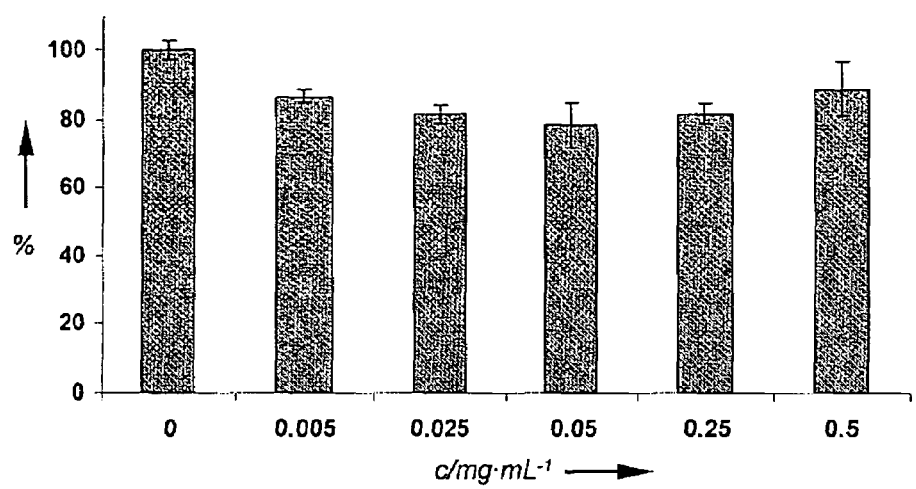
FIG. 2. Cytotoxicity profiles of CdS@tiopronin QDs when incubated with human fibroblasts as determined by MTT assay. Percentage of viability of fibroblasts was expressed relative to control cells (n=3). Results are represented as mean±standard deviations.

Biocompatibility studies of CdS@tiopronin quantum dots were undertaken by evaluating cell viability of hTERT-BJ1 human fibroblasts using two different cell methods. Cell viability staining using calcein AM/ethidium homodimer[11] showed that cells exposed for 24-h to CdS@tiopronin QDs were more than 99% viable. In addition, cell viability was also assessed using the 3-(4,5-dimethylthiazol-2-yl)-2,5-diphenyltetrazolium bromide (MTT) assay.[12] This assay relies on the mitochondrial activity of fibroblasts and represents a parameter for their metabolic activity. The metabolic activity and proliferation of fibroblasts was thus measured after 24 hr culture, and the values reached 80% compared to untreated controls (see FIG. 2).

Figure 3:
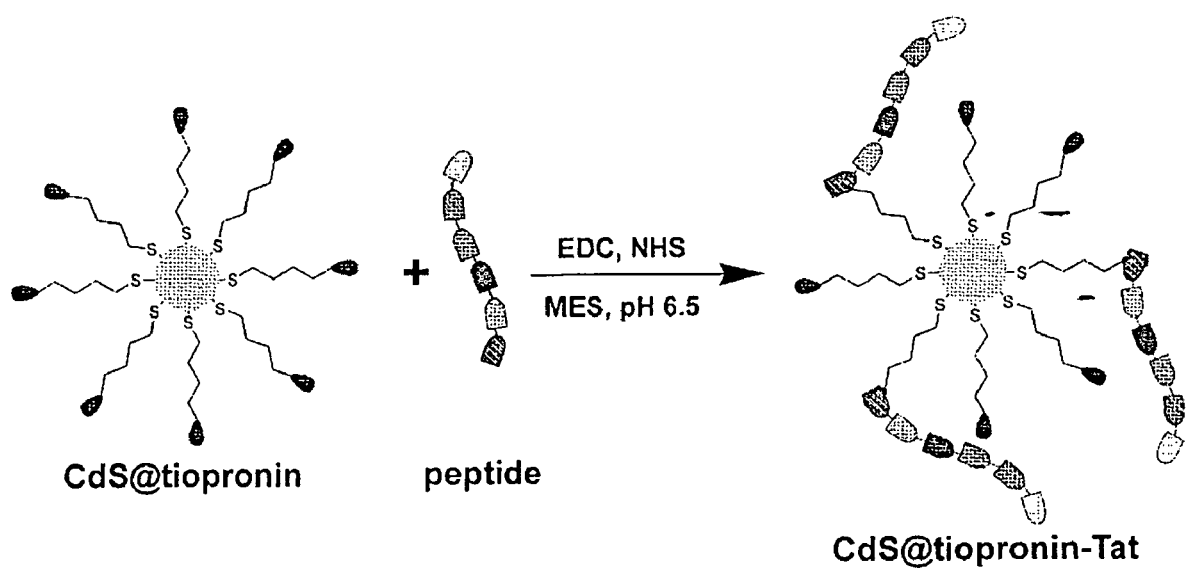
FIG. 3. Synthesis of CdS@tiopronin-Tat.

To demonstrate the utility of CdS@tiopronin quantum dots in cell biology studies, the quantum dots were functionalized with a Tat protein-derived peptide sequence (GRKKRRQRRR). As previously stated the free carboxyl group of the tiopronin is available for covalent coupling to various biomolecules (such as proteins, peptides, and nucleic acids) by cross-linking to reactive amine groups. In addition, this carboxylic layer is expected to reduce passive protein adsorption on quantum dots. This reactivity was used for the functionalisation of the quantum dots with a Tat protein-derived peptide sequence. The reactions utilize the water-soluble carbodiimide, N-[3-(dimethylaminopropyl]-N'-ethylcarbodiimide hydrochloride (EDC),[13] to catalyze reactions between CdS@tiopronin acid groups and Tat protein-derived peptide sequence amine groups. N-hydroxysulfosuccinimide was included in the reaction mixture to improve the efficiency of the carbodiimide-mediated amide-forming reaction by producing hydrolysis-resistant active ester reaction intermediates (FIG. 3). [14]

Figure 4:
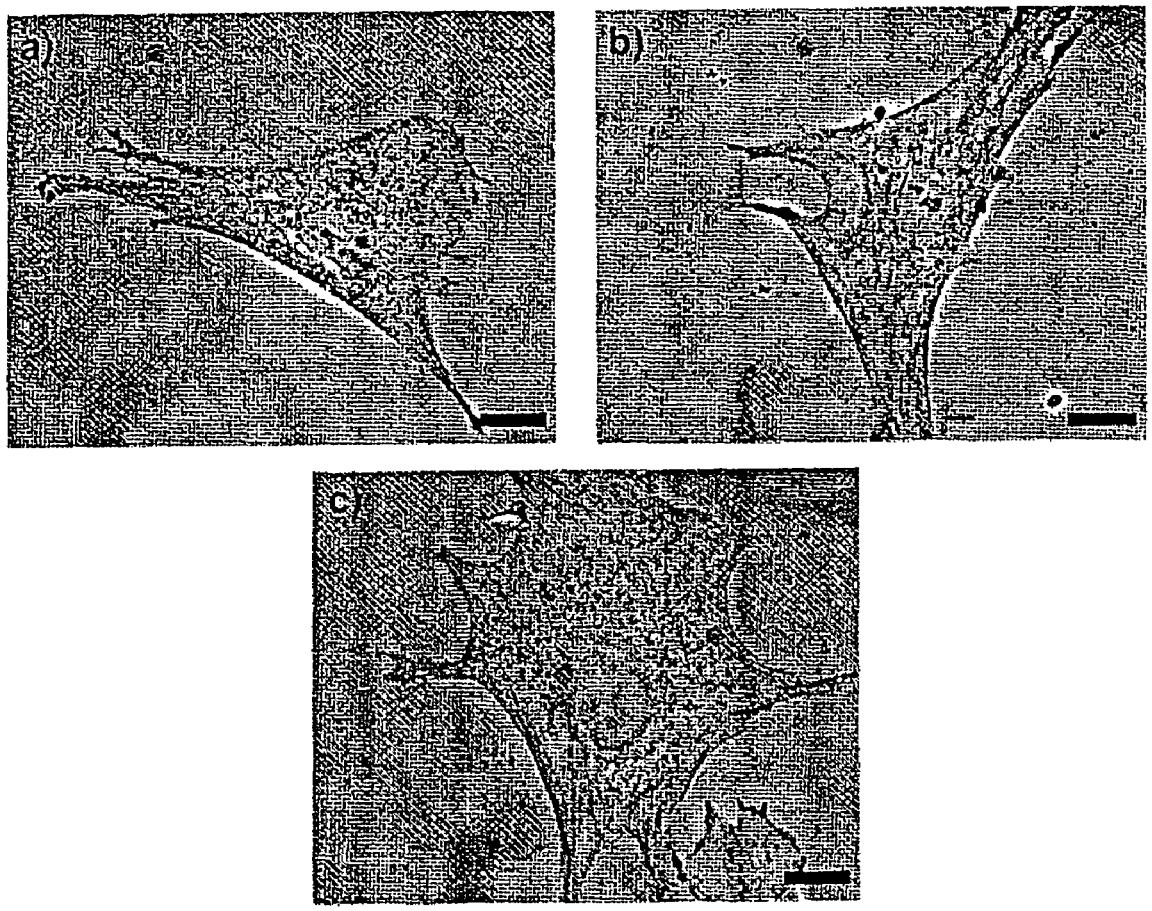
FIG. 4. Overlay of the fluorescence (green) and phase contrast images of: a) hTERT-BJ1 human fibroblasts (control experiment); b) hTERT-BJ1 human fibroblasts incubated with CdS@tiopronin; c) hTERT-BJ1 human fibroblasts incubated with CdS@tiopronin-Tat. Scale bar: 20 μm.

CdS@tiopronin quantum dots coupled to Tat protein-derived peptide sequence were used with the intention to achieve nuclear targeting of the nanoparticles in hTERT-BJ1 human fibroblasts. The CdS@tiopronin-Tat quantum dots were added to a cell suspension for 15 mins. Excess quantum dots were removed by cell centrifugation, and the cells cultured for 24 h. After cell fixation, the general morphology of the fibroblasts incubated with CdS@tiopronin-Tat quantum dots is shown in FIG. 4c. The figure shows that the cells were well spread, with no distinct change in morphology before (FIG. 4a) and after the incubation (FIG. 4c). Fluorescence staining was observed around the cell nucleus, showing the translocation of the CdS@tiopronin-Tat quantum dots to the nucleus. No fluorescence staining was observed when naked CdS@tiopronin quantum dots were incubated with the cells (FIG. 4b).

In conclusion, the results disclosed herein show how quantum dots comprising tiopronin ligands may be prepared using a straightforward and economical methodology. The biocompatibility of these quantum dots is also demonstrated. The functionalization of the quantum dots of the present invention with targeting groups is described using the example of a translocation peptide that allows the quantum dots to penetrate the cell membrane and target the nucleus of cells. This methodology could easily be adapted to conjugate different peptides and proteins to the quantum dots, for example to improve staining methodologies for cell biology studies.

References

The documents cited herein are expressly incorporated by reference in their entirety.

[1] H. Gleiter, *Adv. Mater.* 1992, 4, 474-481
[2] M. Brucher, M. Moronne, P. Gin, Weiss, A. P. Alivisatos, *Science* 1998, 281, 2013-2016
[3] W. C. W. Chan, S. M. Nie, *Science,* 1998, 281, 2016-2018.
[4] H. Mattousi, J. M. Mauro, E. R. Goldmann, G. P. Anderson, V. C. Sundar, F. V. Mikulec, M. G. Bawendi, *J. Am. Chem. Soc.,* 2000, 122, 12142-12150
[5] A. P. Alivisatos, *Pure Appl. Chem.* 2000, 72, 3-9
[6] G. P. Mitchell, C. A. Mirkin, R. L. Letsinger, *J. Am. Chem. Soc.,* 1999, 121, 8122-8123
[7] T. Denneberg, J. O. Jeppson, P. Stenberg, *Proc. Eur. Dial. Transplant. Assoc.,* 1983, 20, 427-433
[8] M. J. Hostetler, J. E. Wingate, C-J. Zhong, J. E. Harris, R. W. Vachet, M. R. Clark, J. D. Londono, S. J. Green, J. J. Stokes, G. D. Wignall, G. L. Glish, M. D. Porter, N. D. Evans, R. W. Murray, *Langmuir,* 1998, 14, 17-30
[9] T. Huang, R. W. Murray, *J. Phys. Chem. B,* 2003, 107, 7434-7440.
[10] L. Spanhel, M. Haase, H. Weller, A. Henglein, *J. Am. Chem. Soc.,* 1987, 109, 5649-5655
[11] C. C. Berry, S. Wells, S. charles, A. S. G. Curtis, *Biomaterial,* 2003, 24, 4551-4557
[12] A. K. Gupta, C. C. Berry, M. Gupta, A. S. G. Curtis, *IEEE. T. Nanobiosci.,* 2003, 2, 255-261
[13] D. F. Detar, R. Silverstein, *J. Am. Chem. Soc.,* 1966, 88, 1013-1019
[14] A. C. Templeton, D. E. Cliffel, R. W. Murray, *J. Am. Chem. Soc.,* 1999, 121, 7081-7089.

We claim:

1. A quantum dot comprising a semiconductor core to which a plurality of ligands are covalently linked, wherein the ligands comprise a tiopronin capping group linked to a targeting group, said targeting group directing the quantum dot to a target selected from the group consisting of tissue type, a cell type and a cellular organelle, wherein the targeting group is selected from the group consisting of a translocation signal peptide, a mitochondrial targeting sequence, a nuclear localisation signal, a perioxisomal targeting signal and a transport protein.

2. The quantum dot of claim 1, wherein the semiconductor core of the quantum dot is formed from a metal sulphide selected from the group consisting of cadmium sulphide (CdS), zinc sulphide (ZnS) and lead sulphide (PbS).

3. The quantum dot of claim 1, wherein the semiconductor core of the quantum dot is formed from CdS.

4. The quantum dot of claim 3, wherein the quantum dot emits light at a wavelength between about 400 nm and about 900 nm.

5. The quantum dot of claim 3, wherein the quantum dot has an excitation wavelength of between about 250 nm and about 600 nm.

6. The quantum dot of claim 1, wherein the mean diameter of the quantum dot is between about 2 nm and about 5 nm.

7. The quantum dot of claim 1, wherein the quantum dot is water dispersable.

8. The quantum dot of claim 1, wherein tiopronin comprises a thiol group though which the tiopronin capping group is covalently linked to the semiconductor core of the quantum dot via formation of a metal-sulphide bond.

9. The quantum dot of claim 1 which comprises at least one further species of ligand.

10. The quantum dot of claim 9, wherein the further species of ligand is selected from the group consisting of a carbohydrate group, a glycoconjugate, a peptide group, a lipid group, a drug or a prodrug and a nucleic acid molecule.

11. The quantum dot of claim 9, wherein the at least one further species of ligand that is covalently linked to the semiconductor core.

12. The quantum dot of claim 9, wherein the at least one further species of ligand that is covalently linked to tiopronin group.

13. The quantum dot of claim 1, wherein the tiopronin capping group comprises a carboxyl group through which the targeting group is covalently linked via a coupling reaction.

14. The quantum dot of claim 1, wherein the targeting group is one member of a specific binding pair.

15. The quantum dot of claim 1, wherein the targeting group is a translocation signal peptide.

16. The quantum dot of claim 15, wherein the translocation signal peptide is a TAT peptide.

17. A composition comprising a population of quantum dots according to claim 1.

18. The composition of claim 17, wherein the composition is lyophilized.

19. The composition of claim 18, wherein the composition comprising the quantum dots is stable in a lyophilized form for a year when stored in the absence of light at 40C.

20. A method of detecting a component of a biological system, the method comprising:
 (a) providing in the biological system a composition of quantum dots, the quantum dots comprising a semiconductor core to which a plurality of ligands are covalently linked, wherein the ligands comprise a tiopronin capping group linked to a targeting group that is capable of interacting with the component of the biological system;
 (b) exposing the biological system to radiation at an excitation wavelength of the quantum dots;

(c) detecting radiation emitted by the quantum dots at their emission wavelength thereby to detect the component in the biological system, wherein the targeting group is a signal group that carries the quantum dot to a component of the biological system, which component is selected from the group consisting of a tissue type, a cell type and a cellular organelle, and wherein the targeting group is selected from the group consisting of a translocation signal peptide, a mitochondrial targeting sequence, a nuclear localisation signal, a perioxisomal targeting sequence and a transport protein.

21. The method of claim 20, wherein the biological systems is selected from the group consisting of an in vivo biological system or an in vitro biological system.

22. The method of claim 20, wherein the targeting group directly interacts with the component of the biological system.

23. The method of claim 20, wherein the translocation signal is a TAT peptide.

24. The method of claim 20, wherein the method is for an immunoassay, a hybridization assay, cytometry or imaging.

25. The method of claim 20, wherein the method is for diagnosing a disease.

26. A method of labelling a component of a biological system, the method comprising contacting the component of the biological system with a composition of quantum dots, the quantum dots comprising a semiconductor core to which a plurality of ligands are covalently linked, wherein the ligands comprise a tiopronin capping group linked to a targeting group, wherein the targeting group is capable of binding to or associating with the component of the biological system thereby to label it, said component being selected from the group consisting of a tissue type, a cell type and a cellular organelle, wherein the targeting group is selected from the group consisting of a translocation signal peptide, a mitochondrial targeting sequence, a nuclear localization signal, a perioxisomal targeting sequence and a transport protein.

27. A method of making composition of quantum dots comprising metal sulphide cores, wherein the metal sulphide is selected from the group consisting of cadmium sulphide, zinc sulphide and lead sulphide, to which a plurality of ligands are covalently linked, wherein the ligands comprise a tiopronin group, the method comprising mixing sodium sulphate, an aqueous solution of tiopronin and a metal nitrate, wherein the metal nitrate is selected from the group consisting of cadmium nitrate, zinc nitrate and lead nitrate, thereby producing the quantum dots in a self-assembly reaction in which thiol groups of the tiopronin covalently link to the semiconductor cores via metal-sulphide bonds.

28. The method of claim 27, wherein the method is single-step procedure.

29. The method of claim 27, wherein mixing step is carried out at room temperature.

30. The method of claim 27, further comprising coupling a targeting group to the carboxyl group of the tiopronin.

31. The method of claim 27, wherein in the coupling step, the carboxyl group of the tiopronin group is coupled to a reactive amine group of the targeting group.

32. The method of claim 27, wherein the coupling step is a carbodiimide coupling reaction in the presence of N-[3-(dimethylamino)propyl]-N'-ethylcarbodiimide hydrochloride (EDC), and optionally N-hydroxysuccinimide (NHS).

* * * * *